United States Patent [19]

Klein et al.

[11] 4,334,027

[45] Jun. 8, 1982

[54] PREPARATION OF IMMOBILIZED ENZYMATICALLY-ACTIVE SUBSTANCE

[76] Inventors: Joachim Klein, Schapenbruch 14, 3300 Braunschweig; Fritz Wagner, Hohe Wiese 2, 3300 Braunschweig-Stöckheim, both of Fed. Rep. of Germany

[21] Appl. No.: 124,573

[22] Filed: Feb. 25, 1980

[51] Int. Cl.$^3$ .................. C12N 11/10; C12N 11/08; C12N 11/04

[52] U.S. Cl. ................................. 435/178; 435/180; 435/182

[58] Field of Search ............... 435/174, 178, 179, 180, 435/182

[56] References Cited

U.S. PATENT DOCUMENTS

| | | | |
|---|---|---|---|
| 3,733,205 | 5/1973 | Shovers et al. | 435/174 X |
| 4,208,482 | 6/1980 | Ehrenthal et al. | 435/178 |
| 4,259,445 | 3/1981 | Glass et al. | 435/178 |

OTHER PUBLICATIONS

Kierstan et al., The Immobilization of Microbial Cells, Subcellular Organelles and Enzymes in Calcium Alginate Gels, Biotech. & Bioeng., vol. XIX, 1977, (pp. 387-397).

*Primary Examiner*—David M. Naff
*Attorney, Agent, or Firm*—Scully, Scott, Murphy & Presser

[57] ABSTRACT

Immobilized enzymatically-active substance is prepared by forming a combination of an enzymatically-active substance and an aqueous polyelectrolyte solution containing a substantial amount of alginate, adding the combination to an aqueous precipitation both containing a source of multivalent ion to form beads of gel containing the enzymatically-active substance, drying the gel beads under controlled conditions to significantly reduce the diameter of the beads and cause hardening of the beads to provide increased mechanical strength, and adding the dried beads to a precipitation both containing a multivalent ion to effect further hardening of the beads. The combination of enzymatically active substance and polyelectrolyte solution may contain an epoxy prepolymer. After further hardening in the polyelectrolyte solution, the beads may be suspended in a buffer solution to dissolve the polyelectrolyte and form porous beads. The process enables manufacture of enzymatically active beads of great mechanical strength, having a high content of enzymatic substance and a high degree of porosity.

26 Claims, No Drawings

PREPARATION OF IMMOBILIZED ENZYMATICALLY-ACTIVE SUBSTANCE

BACKGROUND OF THE INVENTION

Biocatalysts have gained increased importance in the direct recovery of primary and secondary metabolic substances.

Examples in actual practice which can be designated of technological interest for industry comprise:
1. Recovery of fructose from glucose through glucose isomerase.
2. Production of 6-APS from penicillin G through penicillin acylase.
3. Production of L-aspariginic acid from ammonium fumerate through E-coli.
4. Production of L-malic acid from fumerase with ammoniagene cells of brevi-bacterium.

In the technical microbiology, as well as in microbial engineering the term "biocatalyst" is understood to mean a biological system fixed through a macroscopic carrier, which is composed of enzymes or whole cellular microorganisms.

In recent times the use of fixed microorganisms as a biocatalyst has gained added importance and preference due to reduced production costs and improved process flexibility, especially with regard to multi-enzyme reactions.

The production of biocatalysts is essentially carried out by the physical encapsulation of the microorganisms in a polymer matrix.

Depending upon the production method and process design the following materials are used in the manufacture of such matrixes;
Polyacrylamide; Polymethacrylamide; Collagen; Cellulosetriacetate; Carboxymethylcellulose; Agar: Co-Poly-(maleic acid styrol); Carageenen. Biocatalysts produced according to the present state of technology are encumbered with difficulties in their manufacture and biocatalysts produced by such processes are burdened with deficient properties.

Particularly within the group: alginate, CMC, and Copolymer catalysts which are formed in a relatively simple manner by gel formation with multivalent cations, the lack of resistance to phosphate buffer solutions presents a considerable disadvantage wherein numerous reactions are being carried out in such a medium in actual practice.

In the use of natural electrolytes there can occur the danger of microbial attack, which can result in the destruction of the matrix material.

Furthermore, it will be hardly possible to employ these types of catalysts in solid bed reactors because of insufficient strength and tenacity.

The production of the cellulose triacetate catalyst through the intermediary of a wetspin process employs a fixation method which can only be used with few microorganisms because of the highly toxic nature of the utilized solvents, such as toluene or methylene chloride. Additionally, because of its fibrous form, the catalyst is restricted to use in solid bed reactors. The production of collagen catalysts is very complex. Because of the membrane form their use is restricted to spiral reactors. The toxic step due to hardening with glutardialdehyde can not be avoided. Polyacrylamide catalysts, on the other hand, which are the products of block polymerization, are described as sharp-edged, irregular granulates. Their use in stirring reactors evidences their high abrasion, which limits their capacity to be charged with microorganisms. This has been confirmed in the following German Laid-Open patent application:

| DE-OS | 2 252815: | 4.8 g E. coli; catalyst | = 120 ml 4%/vol. |
|---|---|---|---|
| DE-OS | 2 420102 | 17 g cells; catalyst | = 170 ml 10%/vol. |
| DE-OS | 2 414128 | 12 g cells; catalyst | = 120 ml 10%/vol. |

Only a few processes have attained technical importance notwithstanding intense research. This is due to the following deficiencies: The mechanical strength and stability of many carriers is too low to allow the use thereof in large reactors; the fixation process is too complex which renders the use of such catalysts uneconomical; the attainable charging is insufficient, resulting in an unfavorable space/time yield.

One of the widest known processes employs physical encapsulation in a polymer matrix.

Examples are: polyacrylamide; polymethacrylamide; collagen, cellulose triacetate and ionotropic gels. These fixation processes are used because there occurs therein only relatively low deactivation of the enzymes, whole cells or cell fragments. It is known that the encapsulation in ionotropic gels represents a process in which, contrary to polyacrylamide or polymethacrylamide gels, practically non-toxic materials can be employed, as for instance, alginate, $Ca^2$ . . . systems.

M. Kierstein and C. Bucke report in Biotechn. and Bioeng. 19 (1977) page 387, the encapsulation of enzymes, cell fragments and of whole cells in Ca-alginate gels.

These authors prepare the production of fibrous catalysts by injection of an Na-alginate solution into a $Ca^{2+}$ precipitation bath. According to these authors the thus formed fibers exhibit only a marginal stability. A further disadvantage lies in the fact that the fibrous biocatalysts are restricted to their use in solid-bed reactors.

U. Hackel proposes in his dissertation (*) the formation of globular ionotropic gels through injecting the polyelectrolyte solution into a crosslinking bath. This author points out the utility of several other types of polyelectrolytes, including completely synthetic products such as styrolmaleic acid copolymer.

(*)Techn. Universitat Braunschweig 1976, Polymereinschluss von Mikroorganismenzu Aufbau und Reaktivitat von Biokatalysatoren.

However, these proposals have not lead to biocatalysts of sufficient strength and high content on biowetmass. The increase of strength by means of greater polymer content in the biocatalyst cannot be easily achieved because the highly viscous solution cannot be processed efficiently.

SUMMARY OF THE INVENTION

It is the object of this invention to develop a process for the manufacture of biocatalysts which have great strength, evidence a high content of enzymatic substances, and possess a high degree of porosity.

Furthermore, it is another object of the invention to find biocatalysts having a high content of an active substance: (g enzymatically-active substance/ g catalyst beads), and which after gentle drying evidence a shrinkage of 4/5 to 1/5 relative to their original size. Biocatalysts of that type are preferably prepared according to the process set forth in this invention, but are not necessarily restricted to the process therein. Since such catalysts have become known to the technology, the capability for the development of other processes has thus been provided. The basic concept of this invention sets forth that for the first time use has been made of the technical effect that through the gentle drying of the catalyst beads these achieve a predetermined shrinkage which leads to the imparting of high strength and a high content of enzymatic active substance, with a concurrent high degree of porosity. It is a surprising effect of this invention that by renewed equilibration in the precipitation bath (B) or (C) there is caused only a limited reswelling of the catalysts beads. Only this surprising determination has lead to the solution of the object of the invention. This technical effect was certainly not obvious, otherwise it would have already been applied by experts in the technology since a great need for such biocatalysts pursuant to this invention and having the particular inventive characteristics has existed for a considerable length of time. The process of the invention and that for the production of biocatalysts pursuant to the invention is defined in the claims. The sub-claims pertain to preferred embodiments of the process of this invention.

DESCRIPTION OF THE PREFERRED EMBODIMENTS

The technical effect of the process according to the present invention is ascertained from the following example:

Gel beads are produced in a known manner by means of crosslinking an 8% alginate solution with a 2% calcium chloride ($CaCl_2$) solution. Through gentle air drying at room temperature over an interval of 5 hours a particle shrinks from 3.5 mm to 1.5 mm diameter, corresponding to about 2/5 of the original diameter. The diameter of the catalyst beads diminished rapidly up to the first two hours of drying and proceeded thereafter up to 5 hours at a much slower rate. The solids content of the beads during drying increased from about 10% to 80% in 5 hours and appears to reach a certain flat turning point at 1 and 4 hours of drying time which corresponds to about 15% and 70% solids respectively. Between 1 and 4 hours the increase in solids content proceeded at a uniform rate. Overall, the increase in the solids content can be considered to be of a generally uniform rate. The unexpected technical advantage of the process of this invention is given by the fact that renewed equilibration in a 2% $CaCl_2$ solution produces only a limited swelling of the particles to a diameter of about 2 mm. No further swelling took place in a pilot test conducted over a period of six weeks at 65° C., using a 30% glucose solution.

The process of this invention is described in the following examples:

EXAMPLE 1

First the mixture (A) is prepared by suspending 150 g of pressed yeast in 150 ml of water and this enzymatic active substance is then combined with 450 ml of the polyelectrolyte in the form of an 8% by weight aqueous Na-alginate solution.

Used for precipitation bath (B) containing multivalent ions of a charge opposite to that of the polyelectrolyte a 0.2 molar solution of $CaCl_2$.

From a capillary having a 4 mm diameter, in a step or phase 1 the mixture (A) is introduced dropwise into mixture (B) while the latter is being stirred. Bead-like particles are thus formed having a diameter of 4 mm. These are further solidified during an additional residence time of 15 minutes while maintaining agitation.

In a step two (2), the thus formed catalyst beads with the encapsulated enzymatic substance are filtered off and washed with a physiological $NaCl_2$ solution.

In a step three (3) the catalyst beads are subjected to gentle drying in a forced-air oven which is maintained at a temperature of 30° C. Taking place thereby is the shrinkage and hardening of the catalyst beads. This shrinkage in relation to the original bead size prior to drying amounts to about 2/5 of the bead diameter.

After-hardening is carried out in a step four (4) by placing the catalyst beads for 30 minutes in a precipitation bath (C) consisting of a 0.1 molar aluminum sulfate $Al_2(SO_4)_3$ solution.

After washing of the catalyst beads in a step five (5) with a physiological $NaCl_2$ solution, the product is removed in a moist condition.

The catalyst beads prepared according to this example show the following high values of mechanical strength and the following high content of enzymatic active substance.

From the fact that the volume of 600 ml of mixture (A) has been reduced to 170 ml and that in this quantity of catalyst there is now contained the original 150 g of pressed yeast as the biowetmass, there results a charge of 0.88 g pressed yeast/g of biocatalyst. The pressure resistance determined according to the process of this invention was found to be a lead capacity of 750 p/bead at the fracture point.

EXAMPLE 2

Initially the mixture (A) through a suspension of 100 g of moist E-coli ATCC 11105 which has been obtained by centrifuging, is made up with water to a volume of 150 ml., combined with 450 ml of an aqueous Na-alignate solution at 8% by weight as the polyelectrolyte. Further processing takes place as set forth in Example 1.

From the starting volume of 600 ml there is obtained 165 ml biocatalyst beads with an activity of 0.6 g BWM/ml biocatalyst. Pressure resistance of 800 p/bead was obtained by the described process.

EXAMPLE 3

Initially the mixture (A) is made up consisting of 100 mg amyloglucosidase dissolved in 10 ml of an aqueous 8% sodium alginate solution.

For the precipitation bath (B) a 0.5 molar $CaCl_2$ solution is used to provide the mixture (A) with the required multivalent oppositely charged ions.

In step one (1) the mixture (A) is introduced dropwise from a capillary having a diameter of 0.4 mm into mixture (B) as the latter is being stirred so as to form bead-like particles. Further solidification takes place as the charge is maintained for an additional 15 minutes under agitation.

In step two (2) the produced catalyst beads containing the encapsulated enzymatic substance are filtered off and washed with a physiological $NaCl_2$ solution.

In step three (3) the catalyst beads are gently dried by passing an air stream of 30° C. over them for a duration of 20 hours, thus effecting shrinkage and strengthening of the catalyst beads. Their diameter is now about 1.5 mm, corresponding to a relative shrinkage of 2/5 relative to their original size.

After-hardening takes place in step four (4) wherein the catalyst beads are suspended for 30 minutes in the precipitation bath (C) consisting of a 0.1 molar solution of $Al_2(SO_4)_3$, are then subjected in step five (5) to a washing process with a physiological NaCl solution and then removed in a moist condition.

In their final state the biocatalyst beads have a diameter of 1.8 mm which calculates to a content of 32 mg enzyme/ml biocatalysts according to the material balance. The fracture strength determined according to the process of this invention was determined to be 780 p/bead.

The biocatalysts produced according to the present invention exhibit a much improved pressure resistance and a considerably higher content of enzymatic substance, expressed as g enzymatic substance/g catalyst bead in comparison with the conventionally produced biocatalysts. The higher bead rupture strength was determined by comparative testing of non-hardened alginate beads as opposed to biocatalyst beads produced according to the process disclosed in the present invention. The measuring technique for the determination of the rupture strength is described hereinbelow:

The test apparatus is composed of a securely mounted base plate functioning as the specimen receiving table. Vertically arranged relative thereto is a gear-motor-driven piston carrying the anvil with the therein mounted pressure transducer (Hottinger Baldwin Messtechnik, Darmstadt; transducer model U 1/1 pond). The signal from the pressure transducer is transmitted via an amplifier, type KWS 3072 (FMB, Darmstadt) to a recorder.

For measuring the load capacity of the catalyst beads there is used a single bead per test. The piston applies pressure from above as it advances 1.45 mm/minute. The applied force is transmitted over the transducer and amplifier as a direct measuring unit to the recorder in the form of a time/force plot.

Definitive statements regarding the rupture strength can be made from the time/force plot since the curve abruptly discontinues at point of rupture.

The measuring error usually lies below 1% although testing of several beads from one charge shows greater deviation which, however, does not exceed ±5%.

Through this measuring technique, the rupture strength is defined by the value "P/Bead" as the function of the geometry/size relationship of the test bead.

This measuring technique records the force in only one unit value, namely pond/bead; as expressed in the above used term. The unit "pond" is converted to the standard international force unit "Newton" according to: 1000 pond=9.806 Newton. (kg force/cm$^2$=0.010197 Newton).

Through this measuring technique there is ascertained that conventionally produced Ca-alginate beads of 3.5 mm diameter are destroyed by a force of 10–150 p whereas biocatalyst beads produced according to the process as set forth in the present invention and having a diameter of 2 mm are destroyed only at an applied pressure of 600 to 1000 p/bead.

The biocatalysts produced according to this invention contain a high level of biomass arising from the volume reduction by a factor of 3–5 which is unattainable through conventional manufacturing processes.

M. Kierstein and C. Bucke achieved a value of 0.25 BWM/cc of cat. (BWM/=Biowetmass; Cat.-=catalyst).

The German laid-open applications 2 252815; 2 420102; 2 414128 disclose the content of biowetmass as 0.04–0.1 g BWM/cc cat. for encapsulation in polyacrylamide gels.

Biocatalyst beads produced according to the process of this invention, however, show a content of 0.88 g BWM/g cat. The catalyst beads produced according to the process of this invention also evidence a high degree of porosity as shown by pictures taken with the aid of a scanning electron microscope.

The high content of enzymatically active substance is further verified by the conversion of penicillin-G with immobilized E.-Coli cells, amounting to 61% and an absolute activity of 4400 U (units/ltr. cat.).

(Biocatalyst beads of 2.5 mm diameter, BWM content—0.5 g/cm$^3$ Temperature: 37° C.; $c_s$=5%; Penicillin G Na-salt).

EXAMPLE 4

Component ($A_1$) consisting of 30 g E-coli cells ATCC 11105 obtained as a flowable biowetmass by centrifuging are admixed with 10 g of the epoxy resin EPIKOTE Dx255 (German Shell AG, Frankfurt) to form the resin component ($A_2$). 20 g of a 25% aqueous solution of CASAMIDE CA 360 (AKso Chemie, Dueren) representing the polyaminoamide curing component ($B_1$) is now added under vigorous agitation, thereby initiating the polycondensation of the epoxy resin.

The system (D) composed of ($A_2$)+($B_1$)+($A_1$) is now combined with 20 ml of an 8% by weight aqueous Na-alginate solution (Mannucol LD;Alginate Inc. Hamburg). In step one (1) this mixture is injected under pressure from a capillary having a diameter of 0.4 mm into the precipitation bath consisting of a 2% by weight $CaCl_2$ solution so as to form bead-like particles of 3 to 4 mm diameter. After agitation is continued for 20 minutes the now dimensionally stable particles are removed to be washed as in step two (2).

This process is followed in step three (3) by gentle drying in an air stream at 28° C. over a period of 24 hours whereby the catalyst beads shrink to about 2/5 of their original diameter. The dried, fully hardened beads relative to components ($A_2$) and ($B_1$) are washed under stirring for 40 minutes in a 0.1 molar phosphate buffer solution whereby the alginate-polyelectrolyte component is dissolved out of the beads, which reswell to a diameter of about 3 mm. The thus obtained porous biocatalyst exhibits a high content of cellmass and good mechanical stability as shown in the following table.

| Catalyst Type | Content: g BWM/g Catalyst | E. Coli Vol. % | Relative* Activity % | Absolute Activity μ Cat/l Catalyst |
|---|---|---|---|---|
| Irregular particles from block condensation φ 100 μm | 1.24 | 70 | 40 | 80 |
| φ 3–4 mm | 1.24 | 70 | 11 | 16.4 |
| Beads according to the process of the invention; φ 3mm | 1.13 | 67 | 28 | 38 |

*Activity of the encapsulated E. Coli cells relative to the same cell quantity in a free suspension.

At a relative activity of 28% (encapsulated cells vs. an equal number of free cells) the absolute activity amounts to 38 /u Cat. /1 catalyst. (Penicillin G-acylase. 37° C.; ph=7.8) Burst or rupture strength according to the described process is 651 p/bead.

EXAMPLE 5

35 g of pressed yeast, component ($A_1$) are well admixed with 10 g of epoxy resin ($A_2$) (EPIKOTE Dx 255, German Shell AG Frankfurt) and into this mixture 20 g of a 25% by weight aqueous solution of the polyaminoamide curing agent ($B_1$) CASAMIDE CA 360 (Akso Chemie, Dueren) is homogeneously dispersed whereby there is initiated the polycondensation of the epoxy resin.

This system composed of ($A_2$)+($B_1$)+($A_1$) is now well mixed with 35 ml of an 8% by weight Na-alginate solution (D) (Mannucol LD: Alginate Industries, Hamburg) and injected under pressure into a 1% by weight $CaCl_2$ solution (E) using a capillary of 0.4 mm diameter. Thus, bead-like particles are formed having a diameter of 3-4 mm whereupon further processing takes place as is described in Example 1.

The biocatalyst beads ultimately will have a diameter of about 3 mm and the content of biowetmass amounts to 1.18 g/g biocatalyst. The absolute activity, measured by the conversion of glucose to ethanol, equals 0.18 g glucose/ml catalyst.hour.

The rupture strength according to the process of this invention was determined to be 650 p/bead.

The determination of rupture strength (pressure resistance) according to the process of this invention defines this value in the dimension: "p/bead" as a function relative to the geometry of the individual bead. Since the catalyst beads have practically the same shape, a defined unit value for pressure resistance/burst strength is thereby established.

According to the process of this invention, the polymer matrix of a biocatalyst is formed by poly-condensation of a multi-functional water emulsifiable epoxy pre-polymer component ($A_2$) with a multifunctional curing component ($B_1$), such as polyaminoamide. The technical advantage of this common reaction type is given by the fact that polymer formation proceeds at room temperature without the formation of byproducts if and when the preferred reaction components are employed. The polymer matrix prepared according to this invention exhibits high mechanical strength and chemical stability. Treatment with hydrochloric acid as well as contact with media having extreme pH values in either the acid or alkaline range has no adverse effect on the physical properties of the matrix material. According to the process of this invention practically non-toxic biocatalyst beads are produced by means of using epoxy pre-polymers in an aqueous media under absence of harmful solvents.

By direct contact of the moist biomass ($A_1$) with the viscous epoxy resin component ($A_2$), coating of the cells with component ($A_2$) takes place whereby the non-toxic resin takes on the additional function of a protective colloid.

The specific usefulness of epoxides for the encapsulation of whole cells or cell fragments is already demonstrated by the simple block condensation of ($A_2$)+($A_1$) with ($B_1$). The high content of biomass ($A_1$) in relation to the employed quantity of resin and curing agent ($A_2$)+($B_2$) produces porosity in epoxy-polymer material synthesized by block polymerization. This has been verified by examination with the aid of a scanning electron microscope.

In the block polymerization of the carrier materials ($A_2$) and ($B_1$) selected and employed in accordance with this invention, shrinkage takes place with the simultaneous formation of water and this shrinkage leads to a high content of biomass ($A_1$) of great enzymatic activity. However, at a particle size of 3-4 mm required for technical processes, this method yields only low enzymatic activity of about 1/5 of the original as the result of diffusion retardation.

Because of the high content of biomass ($A_1$) not all the substrate molecules come into contact with the cells. This finding is verified by the following experiment: When an epoxy block containing the cellmass is ground in a polymer mill to catalyst particles measuring 50 to 100 microns they exhibit high enzymatic activity. This indicates a relatively mild fixation. The scanning electron microscope results regarding the porosity of the material is also verified.

With increased particle size of such ground catalysts, diminished activity goes hand in hand. Such products are therefore not applicable for use in technical processes. Catalyst beads produced according to this invention, on the other hand, show a high degree of enzymatic activity at a particle size required for employment in technical processes.

The time of up to 30 hours required for room temperature drying and curing of catalyst beads produced according to this invention is also known as "potting time" of the starting materials and, advantageously, provides the time reserve normally desired in technical fixation processes.

The production through conventional methods, on the other hand, is burdened by the high energy demand of the grinding process. Further disadvantages arise from the high degree of attrition of the unevenly dried, brittle particles and the diminished activity caused by diffusion limitation.

These disadvantages are eliminated by the process of this invention and the bead-like shape of the catalyst according thereto.

A porous biocatalyst in bead form is produced by the process of this invention by the combination of polycondensation ($A_2$)+($B_1$) with the formation of ionotropic gels by (D)+($A_1$). Compared with biocatalysts produced by conventional methods, the products of this invention are of high chemical stability and have a high content of enzymatic biomass. The technically important bead form of 2–5 mm size, coupled with a high degree of enzymatic activity and superior strength renders possible their use in various reactor types.

Preferentially the combining of the polyelectrolyte (D), as for instance Na-alginate, with the epoxy-hardener biomass is effected by dropwise injection into the precipitation bath consisting of an aqueous $CaCl_2$ solution. Thereby taking place is an immediate ionic cross-linking of the alginate on the surface which renders possible the formation of the bead-like catalyst. Concurrently there takes place the polycondensation of the resin curing system ($A_2$)+($B_1$) within the Ca-alginate shell. Within a few minutes the drops are solidified into individual beads to allow their removal from the precipitation bath so that they can be washed and dried gently in an air stream so as to cause further hardening. At the end of the drying process at room temperature over a timespan of about 20 hrs. the evenly dispersed alginate is washed out of the catalyst beads using a phosphate buffer solution. In this manner capillary passage ways are created and thus there is formed the porous, bead-like biocatalyst composed of the epoxide ($A_2$)+($B_1$) and the biomass ($A_1$).

The additionally obtained porosity resulting from the encapsulation of the alginate in step three (3) with subsequent removal of step six (6) is noticeable by the swelling of the catalyst beads by more than 30% relative to the dry, alginate-containing product. This is also determinable from the scanning electronmicroscope photographs.

These considerable advantages of the catalyst beads produced according to this invention and the processes set forth therein over those catalyst beads of equal particle size produced by conventional methods is indicated by their considerably higher enzymatic activity.

The technical advantage of enzymatic activity, characteristic for epoxy-biocatalysts produced according to this invention, over conventional products is demonstrated by comparison of penicillin G-acylase activity with fixated E.-coli the results of which are shown in the following table.

Because of the structural changes of the epoxy network, or matrix originating from the polycondensation of (A)+(B) in a polyelectrolyte matrix (D)+(E), the macroscopic material state of the carrier matrix in block condensation particles is changed from a brittle character into elastic behavior in catalyst beads which have been prepared in accordance with the invention. This technical advantage is of utmost importance for the universal employment of the catalyst beads prepared in accordance with the teachings of this invention.

The following table shows the technical superiority of catalyst beads prepared according to this invention over conventional catalysts with regard to burst or rupture strength/pressure resistance:

| Carrier System 1 to 4 see footnote | Pressure Resistance P/bead |
|---|---|
| Polyacrylamide (1) | 10 |
| Polymethacrylamide (2) | 30–80 |
| Copoly-Maleic acid Styrol (3) | 200–400 |
| Epoxy-block (4) | 1000 |
| Epoxy beads this invention | 650–895 |

Catalyst beads prepared according to this invention show no attrition when used even under extreme conditions in batch-wise operation using agitator-equipped reaction vessels.

(1) P. Schara; Dissertation Techn. University, Braunschweig, 1977
(2) As (1) above
(3) U. Hackel; Dissertation Techn. University Braunschweig, 1976
(4) Unpublished experiments with Epoxy-block, current state of technology.

For comparative purposes the following table lists the values of pressure resistance-burst strength p/bead for conventional ion exchange resins, which were determined by the measuring technique as described herein above:

| Product: | LEWATIT; Commercial product, Bayer Ag. Leverkusen |
|---|---|
| Material: | Styrol-divinyl-benzene (DVB) Content on DVB denotes degree of crosslinking |

| Type Designation | DVB % | Pressure Resistance = p |
|---|---|---|
| Macroporous | | |

| Product: | LEWATIT; Commercial product, Bayer Ag. Leverkusen |
|---|---|
| Material: | Styrol-divinyl-benzene (DVB) Content on DVB denotes degree of crosslinking |

| Type Designation | DVB % | Pressure Resistance = p |
|---|---|---|
| Lewatit | SPC 108/H | 8 | 380 |
| Lewatit | SP 112 | 12 | 710 |
| Gel Form Lewatit | SC 104/H | 4 | 50 |

This comparison verifies the high pressure resistance-burst strength of catalyst beads produced according to this invention.

The measuring technique employed has been described earlier in the text of this application.

The extended enzymatic stability of biocatalysts is a very important prerequisite for their successful use under industrial conditions. A biocatalyst produced in accordance with the teachings of this invention consisting of epoxy-encapsulated E.-coli cells in bead form, retained from 21% of its original activity when stored for 120 days in a 0.9% NaCl solution which was maintained at a temperature of 9° C., whereas free cells, stored under identical conditions, became useless after already 3–4 days.

A reaction-kinetic stability test was conducted in a whirl-bed reactor with an agitation device. For this test there were employed freshly prepared catalyst beads according to the present invention. A series of repetitious batch reaction runs was conducted. One liter of a 0.5% pennicillin-G solution was circulated continuously through the catalyst beads containing E.-coli cells as the enzymatically active substance. Temperature: 37° C. pH=7.8

The reaction solution was replaced every 24 hours with fresh 0.5% penicillin-G solution. The enzymatic activity of the biocatalyst remained practically constant for a duration of 30 days. By comparison, the stability test conducted with a polyacrylamide biocatalyst with encapsulated E.-coli cells gave a halflife value of 17 days at 40° C. In this regard, reference is made to: Continuous production of 6-aminopenicillinanic acid from penicillin by immobilized microbial cells; Sato, Tosa & Chibata; European J. Appl. Microbiology, 2, 153–160 (1976).

The special characteristics of the biocatalysts produced according to this invention, especially by the preferred processes described therein, satisfy the requirements for high mechanical strength and chemical stability as well as the needed porosity, coupled with a high enzymatic activity and large cell content.

The bead form of the biocatalysts produced according to this invention affords universal employment thereof in the various reactor types at a high space/time yield with exceptional lifetime stability.

The superiority of biocatalysts produced according to this invention over conventional products is thereby clearly established.

These unexpected manifestations of numerous technical advantages are the result of considerable innovative ingenuity. Of further mention is the simplicity of process, detailed in this invention, as contested with the conventional methods. Economic advantages are further imparted by the less costly starting materials employed in the process of this invention. Furthermore, the broad choice in the selection of the polymer components and crosslinkers afford additional benefits. It has now become feasible to optimally tailor-make ionotropic gels so as to satisfy the physiological characteristics of the biomass.

The extent of the variability is further exemplified by the possibility of using either whole cells, cell fragments or enzymes as the biomass, and this at an advantageously high shelflife for the biocatalysts prepared according to this invention. It was found for instance, that encapsulation of amyloglucosidase in Fealginate catalyst beads retained activity of over 90% after aging for six (6) days.

An additional technical and economic advantage of the process of this invention and the biocatalysts produced in accordance thereto is given by the fact that the cross-linking in ionotropic gels is reversible so that the polymer components of the biocatalysts at the end of their use in technical processes may be readily recovered.

What is claimed is:

1. In a process for producing an immobilized enzymatically-active substance in which an enzymatically-active substance in combination with an aqueous polyelectrolyte solution comprising a substantial amount of alginate is added to an aqueous precipitation bath containing a source of multivalent ion having a charge opposite to that of the polyelectrolyte so that said polyelectrolyte precipitates to form beads of gel containing said enzymatically-active substance wherein the improvement comprises:
   (a) drying of the precipitated beads of gel under controlled conditions as to significantly reduce the diameter of the beads, thereby hardening said beads and imparting to said beads significantly increased strength and a higher ratio of the content of enzymatically-active substance to the diameter of the beads; and
   (b) adding the beads resulting from step (a) to a precipitation bath containing a multivalent ion having a charge opposite to that of the polyelectrolyte to effect further hardening of the beads.

2. A process as in claim 1 wherein said alginate is present in a concentration range of 0.5 to 15 percent by weight.

3. A process as in claim 1 wherein said precipitation bath consists of water and a compound, which is the source of said multivalent ion, in a concentration of 0.5 percent to 35 percent by weight.

4. A process as in claim 1 wherein said beads are allowed to reside in said precipitation bath for a time of from about 5 minutes to about 4 hours.

5. A process as in claim 1 wherein said beads are particles of from about 0.5 mm to about 5 mm.

6. A process as in claim 1 wherein said beads are capable of withstanding pressure of from about 600 ponds/bead to about 1000 ponds/bead.

7. A process as in claim 1 wherein said beads are dried for a period of up to about 30 hours.

8. A process as in claim 1 wherein said beads are dried at a temperature of up to about 80 degrees centigrade.

9. A process as in claim 1 wherein said precipitation bath of step (b) contains said multivalent ion in concentration of from 0.5 to 5 percent by weight.

10. A process as in claim 1 wherein said beads are shrunk as a result of said controlled drying from about 0.8 to about 0.2 of their original size.

11. A process as in claim 1 wherein said enzymatically-active substance is combined with said polyelectrolyte solution in an amount sufficient to form 0.5 gram of enzymatically-active substance per ml. of polyelectrolyte solution.

12. A process as in claim 1 wherein said enzymatically-active substance is chosen from the group consisting of whole reproductive cells, whole non-reproducible cells, cell fragments, and isolated enzymes.

13. A process as in claim 1 wherein said oppositely charged multivalent ion source is chosen from the group consisting of $CaCl_2$, $(Al(SO_4))_3$, and $Fe(NO_3)_3$.

14. A process as in claim 1 wherein said polyelectrolyte solution is a 2 percent to 10 percent by weight aqueous Na-alginate solution, said precipitation bath used to form the beads is a 0.05 to 1 molar $CaCl_2$ solution, and said precipitation bath of step (b) is a 0.05 to 1 molar $Al(SO_4)_3$ solution.

15. A process as in claim 1 wherein said precipitation bath of step (b) is a 0.05 to 1 molar solution of $Fe(NO_3)_3$.

16. A process as in claim 1 wherein said enzymatically-active substance is combined with a resin component of epoxy prepolymer prior to combining with said solution of polyelectrolyte in a resin to enzymatically-active substance weight ratio of from 0.5:1 to 5:1.

17. A process as in claim 16 wherein a hardening agent is added to said combination of enzymatically-active substance and resin component to form an admixture in a weight ratio of from 0.2:1 to 0.8:1 of hardening agent to combination of hardening agent plus resin component.

18. A process as in claim 17 wherein the weight ratio of said admixture to said polyelectrolyte solution is from 1:0.6 to 1:2.8 before precipitating said mixture.

19. A process as in claim 18 wherein the beads precipitated in said precipitation bath are allowed to reside in said bath for a time of from 5 minutes to 50 minutes.

20. A process according to claim 16 wherein said resin component is chosen from the group consisting of water-emulsifiable low viscosity epoxy resin prepolymers having an epoxy equivalent weight (EEW) of 182–212 and a specific gravity of 1.05 at 20 degrees centigrade.

21. A process according to claim 17 wherein said hardening agent comprises viscuous polyaminoamide in an aqueous solution of from 20 to 50 percent by weight of viscuous polyaminoamide.

22. A process according to claim 21 wherein said polyaminoamide has an amino content of 130–160 mg KOH/G, a viscosity of 300–500 poises at 25 degrees centigrade, and a solids content of 50±11 percent.

23. A process as in claim 19 wherein said beads are dried under said controlled conditions so as to effect covalent crosslinking of said epoxy resin as well as reducing the size of the diameter of said beads.

24. A process as in claim 23 wherein said beads from step (b) are further suspended in a phosphate buffer solution whereby said polyelectrolyte is dissolved to form porous epoxy beads under limited reswelling.

25. A process according to claim 16 wherein the porosity of said beads are effected by varying the concentration of said polyelectrolyte, said resin, and said enzymatically active substance during the bead forming step.

26. Immobilized enzymatically-active substance produced according to claim 1 or 17.

* * * * *